United States Patent [19]
Chou

[11] Patent Number: 5,486,171
[45] Date of Patent: *Jan. 23, 1996

[54] TRANSPARENT CAP FIBER OPTICA LASER BEAM ANGLE DELIVERY DEVICE

[75] Inventor: Marilyn M. Chou, Piedmont, Calif.

[73] Assignee: Xintec Corporation, Oakland, Calif.

[ * ] Notice: The portion of the term of this patent shall not extend beyond the expiration date of Pat. No. 5,354,294.

[21] Appl. No.: 319,954

[22] Filed: Oct. 7, 1994

Related U.S. Application Data

[63] Continuation-in-part of Ser. No. 87,981, Jul. 7, 1993, Pat. No. 5,354,294, and a continuation-in-part of Ser. No. 67,566, May 26, 1993, and a continuation-in-part of Ser. No. 14,814, Feb. 8, 1993, Pat. No. 5,366,456.

[51] Int. Cl.⁶ .................................................. A61B 17/32
[52] U.S. Cl. .................. 606/16; 606/16; 606/17; 606/11
[58] Field of Search .................... 606/10, 11, 12, 606/15, 16, 17

[56] References Cited

U.S. PATENT DOCUMENTS

| | | | |
|---|---|---|---|
| 4,445,892 | 5/1984 | Hussein | 604/101 |
| 4,718,417 | 1/1988 | Kittrell et al. | 606/15 |
| 4,740,047 | 4/1988 | Abe . | |
| 5,242,438 | 9/1993 | Saadatmanesh et al. | 606/15 |
| 5,354,294 | 11/1994 | Chou | 606/16 |
| 5,366,456 | 11/1994 | Rink et al. | 606/16 |

FOREIGN PATENT DOCUMENTS

| | | | |
|---|---|---|---|
| 0195375A3 | 9/1986 | European Pat. Off. | A61B 17/220 |
| 4030240A1 | 2/1991 | Germany | H01S 3/082 |
| WO89/00408 | 1/1989 | WIPO | A61B 17/220 |
| WO89/11834 | 12/1989 | WIPO | A61B 17/36 |
| WO92/08427 | 5/1992 | WIPO | A61F 9/00 |
| WO93/03678 | 3/1993 | WIPO | A61B 17/36 |
| WO93/12728 | 7/1993 | WIPO | A61B 17/36 |

*Primary Examiner*—Stephen C. Pellegrino
*Assistant Examiner*—Sonya Harris-Ogugua
*Attorney, Agent, or Firm*—Ray K. Shahani; James J. Leary

[57] ABSTRACT

The present invention relates generally to a family of fiber optic laser beam angle delivery devices for use in medical procedures such as a laser assisted transurethral resection of the prostate (TURP) and other applications, and more particularly, to such devices wherein the transmitted radiation is delivered through and at various angles to the central axis of an optical fiber by refraction or reflection off of a reflective insert or other reflective layer placed adjacent to and in intimate contact with the tip of the optical fiber, the tip assembly being encased by a quartz or other transparent material cap, the transparent cap being held secusely in place by an attachment means.

42 Claims, 4 Drawing Sheets

TRANSPARENT CAP FIBER OPTICA LASER BEAM ANGLE DELIVERY DEVICE

REFERENCE TO RELATED APPLICATION

This is a continuation in part of patent application Ser. No. 08/087,981 filed Jul. 7, 1993, now U.S. Pat. No. 5,354,294, and a continuation in part of patent application Ser. No. 08/067,566 filed May 26, 1993 and a continuation in part of patent application Ser. No. 08/014,814 filed Feb. 8, 1993, now U.S. Pat. No. 5,366,456, all three of which are hereby expressly incorporated herein, in their entirety, by reference.

FIELD OF THE INVENTION

The present invention relates generally to a family of fiber optic laser beam angle delivery devices for use in medical procedures such as a laser assisted transurethral resection of the prostate (TURP) and other applications, and more particularly, to such devices wherein the transmitted radiation is delivered through and at various angles to the central axis of an optical fiber by refraction or reflection off of a reflective insert or other reflective layer placed adjacent to and in intimate contact with the tip of the optical fiber, the tip assembly being encased by a quartz or other transparent material cap, the transparent cap being held securely in place by an attachment means.

BACKGROUND OF THE INVENTION

Although the first useful lasers were developed in the 1960s, recent advances in laser and fiber optic delivery systems have greatly enhanced the use of this technology in the field of medicine. Today there are numerous types of laser systems designed for operation in a wide range of applications primarily related to surgical and other medical procedures.

A common type of laser known as a CO2 laser delivers radiation with a wavelength of 10.64 microns. However, in order to focus or channel the radiated energy produced by a CO2 laser it is necessary to configure sets of mirrors in certain ways. These systems are typically large and expensive. With the advent of the Nd:YAG type laser delivering electromagnetic energy at a wavelength of 1.064 microns, it became possible to generate and focus the laser radiation through a silica core optical fiber. Thus, fiber optic surgical tools have become important in certain procedures. The range of their utility is still being explored and discovered.

Laser fibers are used in different ways, including incision, necrosis or killing of live tissue, excision or removal of tissue and structure, and cauterization of tissue. A very focused beam would provide the greatest amount of control during either operation. Cauterization and necrosis of living tissue is accomplished by coagulation, or more precisely with respect to the laser itself, by photocoagulation of contacted or penetrated tissue. In this process the laser beam causes the proteins in the contacted tissue to heat up rapidly and thermally denature. This essentially kills living tissue and seals blood vessels. The process has been likened to frying an egg. In practice, during an incision procedure cauterization of the incised tissue is likely to occur simultaneously. Thus, laser surgery is often characterized by an absence of bleeding during the surgery.

In the prior art there are described devices which generate a dual wavelength beam of radiation and effect both cutting and cauterizing simultaneously. Such devices generally use one type of laser with some type of harmonic generator for providing half or double fundamental wavelength beams. There also exist inventions which deliver energy at much shorter wavelengths, such as 250–350 nm. At these wavelengths proteins, as opposed to water molecules, absorb the radiation. These systems, however, are less suitable for general types of surgical operations since they are more complicated to operate. Use of such systems has not become standard in most medical facilities and their cost is generally too high to justify their purchase for occasional use in fairly specialized procedures.

The construction of optical fibers used in surgical procedures is fairly simple. A quartz, plastic or silicone cladding is used to constrain the laser light to the quartz core. Theoretically, only a few of the entering photons are directed straight down the axis of the fiber. Transmission of the radiant beam is possible since the rest of the photons are constrained to the core of the fiber due to internal reflectance by the quartz cladding interface. Very few photons escape the fiber. The technology related to the use of silica core fibers in medical lasers is well known, e.g. B. P. McCann, Photonics Spectra, May 1990, pp 127–136.

Differences between these types of optical fibers and those used in telecommunications and data transmission are important. Several design factors must be considered such as sterilizability, quartz core integrity and purity, power capacity and index of refraction of materials of construction.

Generally, 10 to 100 watts of energy are used to perform soft tissue surgery. A fiber optic laser scalpel used externally might be operated much differently than one used in internal or endoscopic surgery. Some endoscopes have multiple channels to accommodate a viewing port or camera, a laser delivery device, and an irrigation supply and accompanying vacuum channel.

Delivery of high power radiation can have a very damaging effect on the fiber tip itself. One of the problems with existing designs is that the tip which directs the laser beam to a right angle becomes overheated. This is caused by an absorption of power (heat) at the reflecting surface. Overheating at or near the surface of the fiber tip can be caused by an accumulation of incompletely burned tissue which rapidly heats up and triggers a process known as thermal runaway. As heat builds up, the fiber tip gets hot and sometimes stats to melt or deform. Often, angle firing fiber optic surgical devices will need to be replaced partway through the surgical operation due to this problem.

Thus, the problems associated with currently available angle delivery fiber optic laser devices are mainly related to fiber overheating and failure. One solution would be to provide a transparent, hard, heat resistant cap over a highly reflective surface in the scalpel tip for deflecting the beam, the cap thus protecting the tip and being highly durable and resistant to thermal damage.

This invention discloses a device wherein the end of the optical fiber is bias cut and, optionally, polished. The tip of the fiber can be placed adjacent to or in intimate contact with a highly reflective mirrored surface. This surface would most likely be a metallic or other reflective material as an insert in the tip assembly or as a layer applied to the tip of the fiber. Depending on the application and operational parameters the instrument is designed around, it may be advantageous to bury the bias cut tip of the optical fiber into the reflective mirrored surface of the reflective cap or insert. Thus, the supplied laser radiation is reflected to the side and leakage of light near the interface between the fiber and the reflective surface is reduced or eliminated. Another embodiment of this invention provides the firing tip with a void or pocket of air at the end of a bias cut fiber. A protective cap made of some material transparent to the laser radiation is applied over the reflective tip or tip assembly to protect the tip from fouling or debris and also to provide a highly durable device at high temperatures and duty cycle.

An embodiment which has proven to be very effective is a truncated ball tip fiber having a bias cut through the ball portion providing a cut surface with a greater surface area than that of the fiber alone. When the tip is cut at an operative angle and polished, a laser beam is reflected internally to the side. The polished end surface can be placed in intimate contact with an efficient reflector such as a mirrored surface having a layer of gold or silver or other metal or material. The result would be to reflect any part of the laser beam which passed through the cut end surface and was not internally reflected. Additionally, the cut surface of the ball tip can be recessed or buried slightly in the reflective surface resulting in a device which transmits the laser beam in a defined angle without overheating or failing.

Another embodiment might have a reflective layer deposited directly onto the cut surface of the fiber. One material capable of being deposited in a very thin coating and producing a very high reflectance is gold. A protective layer over the reflective material could also be applied and be useful to add durability and thermal resistance to the reflective material. U.S. Pat. No. 4,992,087, incorporated herein by reference, discloses a reflective coating consisting of a metal or metal alloy and a process for applying it to a glass surface.

Multiple layer optical interference films, also known as interference filters or films, are well known in the art. Such films comprise alternating layers of two or more materials, typically one with a relatively high index of refraction and the other with a relatively low index of refraction. These materials are also known as dielectrics. Such are well known in the art and can be designed to reflect or transmit light radiation from various portions of the electromagnetic spectrum. Often, materials with high and low indices of refractivity are applied in alternating layers so as to comprise a "quarter wave stack", each layer having an optical thickness equal to approximately one quarter wavelength of the incident light wave. These types of reflectors have been described providing optical absorption losses of as little as 0.0001% to 0.0002%.

Methods for manufacturing these films are described in the prior art. U.S. Pat. No. 4,925,259, incorporated herein by reference, describes a damage-resistant dielectric coating formed over a silica substrate. Using a pulsed-plasma assisted chemical vapor deposition process several hundreds and even thousands of layer pairs can be deposited rapidly. Larger differences between the indices of refraction require a lesser number of layer pairs to obtain a given value of reflectance. In some cases, the indices of refractivity of alternating materials can be very similar and the number of layers very great. These coatings seem to have superior damage-resistance to optical radiation, approaching the damage resistance of pure silica. For laser applications using high power, components can be made to withstand high energy flux densities. They are also resistant to abrasion. Since the materials are very similar in composition there are fewer problems associated with differences in thermal and mechanical properties. Peeling and scaling is avoided as are microcracks which, in a given layer, could otherwise occlude the film.

Clinical applications for this invention include surgical ablation, vaporization, incision, excision, coagulation and cauterization of tissue. These operations can be performed in air or in fluid, either in open or in endoscopic methods, through natural body channels or through artificial incisions. Other applications include scientific industrial, entertainment, communications, and other commercial applications where angle delivery of laser beams via optical fibers at any wavelength is useful.

SUMMARY OF THE INVENTION

This invention, a transparent cap fiber optic laser beam angle delivery device, comprises an optical fiber, the fiber having: a receiving end, a central axis, and a transmitting end, the transmitting end having a bias cut end surface, the bias cut end surface defining a predetermined operative angle with the central axis of the fiber. The device also comprises a transparent cap, with the transmitting end disposed within the transparent cap such that the transmitting end of the optical fiber is protected from exposure to operating debris and fluids, and an attaching means, the attaching means securing the transparent cap to the fiber.

In preferred embodiments of the invention, the transparent cap is made of quartz, polymeric material, or any material which allows the transmission of laser radiation. The end surface of the transmitting end could lie in a plane at an angle of approximately 45 degrees to the central axis, at an angle greater than 45 degrees with respect to the central axis or at an angle less than 45 degrees with respect to the central axis. Furthermore, the bias cut end surface of the fiber could be contoured, for instance with a concavity or convexity, such that a beam with a predetermined beam pattern is delivered.

In preferred embodiments, the attachment means creates a sealed chamber within the cap within which the bias cut end surface is disposed. The chamber could be filled with a fluid, a liquid, a gas, or it could be evacuated.

In preferred embodiments, a reflective coating is applied over the bias cut end surface of the transmitting end of the optical fiber. This reflective coating could consist of a dielectric material, a metallic material, or it could consist of a plurality of layers of different materials, the materials having different indices of refraction.

In preferred embodiments, the transparent cap further comprises an insert member having a reflective surface. The bias cut end surface of the optical fiber could be in intimate contact with the reflective surface of the insert member. The insert member could be composed of a metallic material, or any other suitable, durable, material with a reflective surface thereon.

In preferred embodiments, the fiber tip is enlarged proximate the transmitting end providing a truncated ball shaped or elongated ball shaped transmitting end, thus providing the bias cut end surface with an increased area. The reflective surface of the insert could be provided with a recess such that the bias cut end surface of the fiber is disposed within the recess.

In preferred embodiments, the attaching means comprises a bushing disposed between the transparent cap and the optical fiber. This bushing could be composed entirely out of flexible materials, or it could be composed out of any other combination of materials which would maintain the narrow profile of the device yet attach the cap to the fiber securely and effectively, especially during operation.

In preferred embodiments, at least one point on the transmitting end of the optical fiber is in intimate contact with the transparent cap. The transmitting end of the optical fiber could be fused to the transparent cap, thus providing an undisrupted optical path. This would eliminate any radiation loss, scatter, or reflective or refractive anomaly or phenomenon otherwise occurring as the radiation passes from the bias cut tip of the fiber through the transparent cap of the invention.

Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF THE INVENTION

The embodiments described herein are referred to as transparent cap, and more specifically as quartz cap reflectance devices, referring to their ability to deliver infrared or other laser radiation by reflectance from one or more surfaces, including surfaces on a reflective insert as well as on the fiber itself through a transparent cap.

Figure 1:
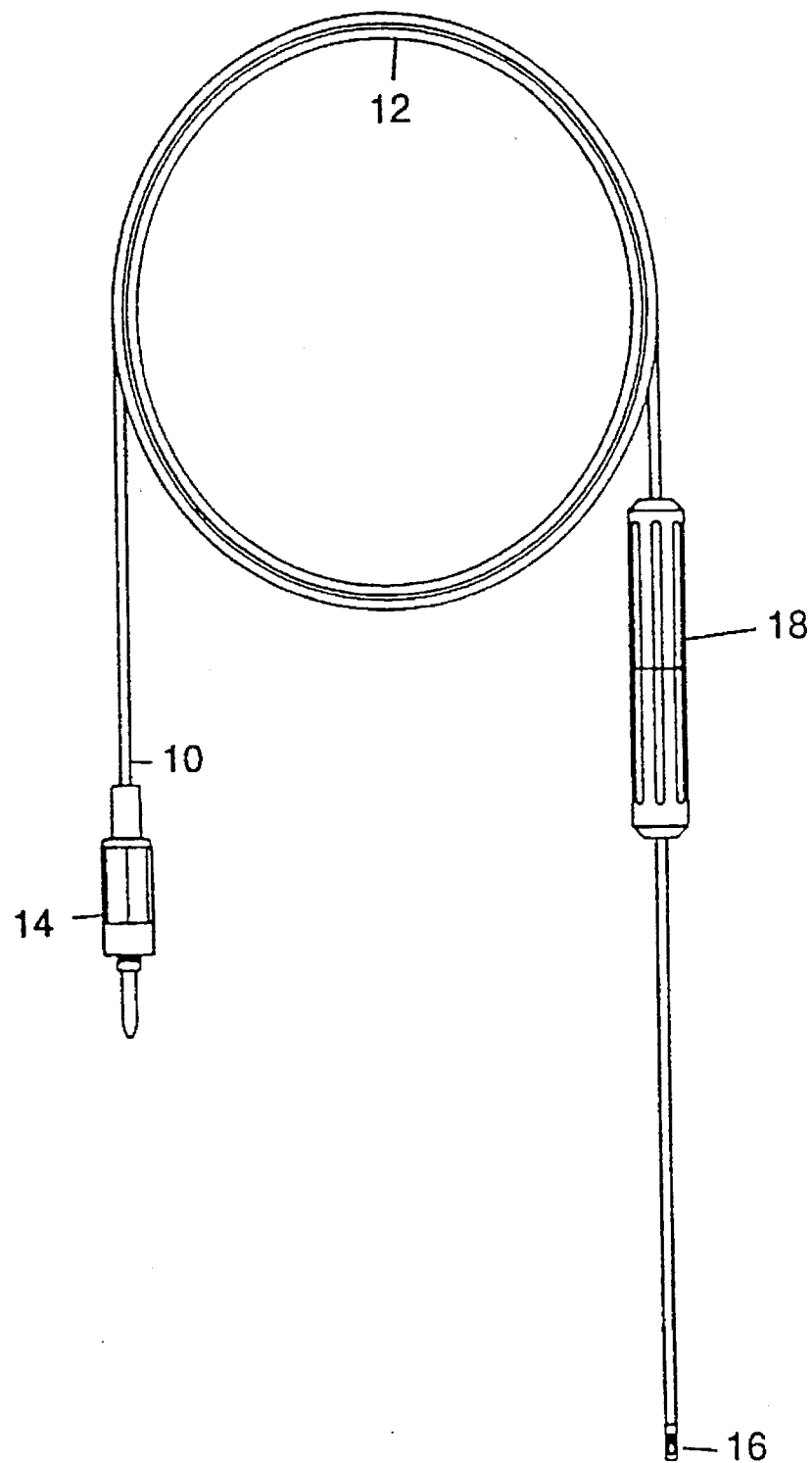
FIG. 1 is a schematic illustration of the present invention in combination with a connector for the optical fiber and associated accessories.

FIG. 1 is a schematic illustration of the present invention in combination with a connector for the optical fiber and associated accessories. At the receiving end 10 of the optical fiber 12 there is a releasable optical fiber connector 14. These connectors are standard in the industry and can also be proprietary. The fiber has an angle delivery tip 16.

Also shown is a positioning apparatus 18 for use when the device is inserted through the lumen of a viewing scope for certain types of procedures. The distance through which the fiber tip is inserted into a cannula or channel of an endoscope can be adjusted and precisely positioned by the surgeon during a surgical operation. It can also serve as a handle or gripping system for the fiber in microprocessor based automated procedures. One such apparatus would be made of two sections which screw together to tighten around the jacket of the optical fiber or untightened for repositioning with a slight twist.

Figure 2:
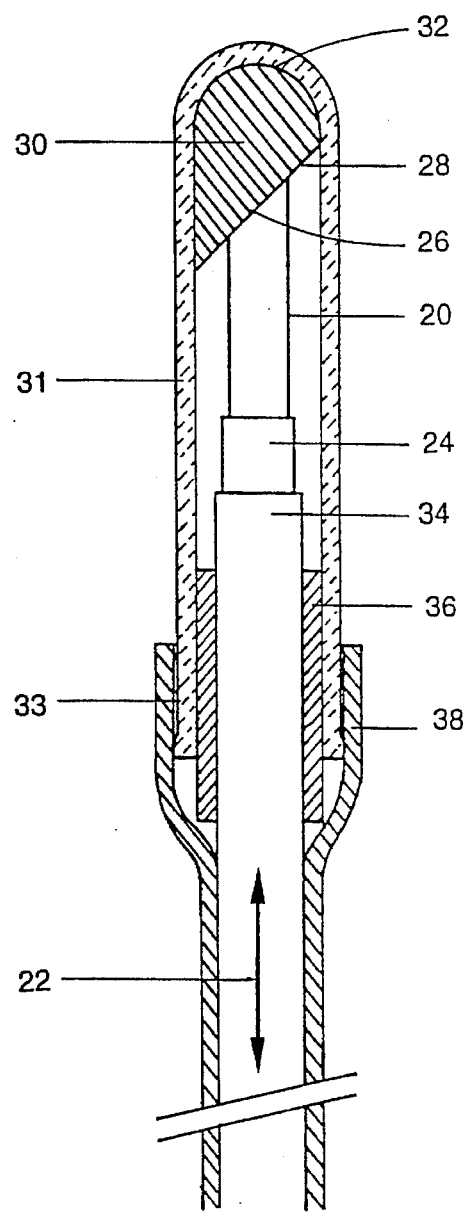
FIG. 2 is a cross section view of the transmitting end of a preferred embodiment of the invention, showing specifically the transparent cap over a reflective insert.

FIG. 2 is a cross section view of the transmitting end of a preferred embodiment of the invention, showing specifically the transparent cap over a reflective insert. As shown, the distal fiber tip 20 is bias cut, i.e. cut at an angle other than perpendicular to the central axis 22 of the fiber. The cladding of the fiber 24 is removed near the distal fiber tip. The bias cut end surface of the fiber 26 is in intimate contact with the mirrored reflective surface 28 of insert 30. The transparent cap 31, having a proximal end 32 and a distal end 33, covers the reflective insert and tip of the fiber, thus providing protection to the tip assembly. This cap can be made out of quartz or processed quartz, or alternatively, some other material or combination of materials. The term transparent is used throughout this document to refer to the optical effect of the cap upon the transmitted laser radiation. Any material suitable for and allowing the transmission of laser radiation without the tip assembly being adversely affected due to heat or thermal deformation or occlusion during operation could be used.

The bias cut end surface of the optical fiber can be adjacent to, nearby or in intimate contact with the reflective surface of the insert member. When the fiber is kissing, or touching, the reflective insert, a combination of reflectance and refractance occurs which results in almost complete lateral transmission of the incident radiation. The surfaces in contact with each other could be bias cut or angled at various specific angles with respect to the central axis, or alternatively, complementarily contoured so as to provide a beam with a specific pattern. For example, the polished tip of the fiber, while cut at an angle to the fiber's central axis, might have a generally convex shape in intimate contact with a reflective cap with a corresponding concavity, or vice versa. This Would result in a beam which focused at a point beyond the fiber and then thereafter became divergent, or, conversely, was ever broadening after reflectance at the reflective surface. Contoured surfaces might be spherical, parabolic, ellipsoidal, etc.

In the embodiment shown in FIG. 2, the transparent cap is placed over the optical fiber and extends over and past the end of the optical fiber outer jacket 34, which covers the fiber cladding, portions of both of which have been removed partially. A bushing 36 is installed over the jacket of the fiber such that, as shown, the transparent cap fits over the bushing and the cap is in contact with the bushing. Finally, a cap securing element 38 covers the junction such that the cap is firmly attached to the fiber. This cap securing element, as shown, can be a section of rubber, plastic, metal, or other material which serves to secure the transparent cap in place over the optical fiber. Thus, the distal end of the transparent cap is disposed between the cap securing element and the bushing. This cap securing element can also be referred to as an outer securing element in as much as the element is external to both the fiber and the cap. Additionally, a layer of adhesive or some other bonding material 39 can be applied between the cap and the outer securing element. It is important that the end of the cap is biased against the insert against the end of the fiber so as to ensure as complete a transmission of the incident laser radiation off of the reflected surface as possible. The cap is held in place by the bushing and the outer securing element. The materials used for the various components such as the bushing and the outer securing element can be changed or modified for various applications, including using all flexible components, etc. The bushing can be rubber, silicone, plastic, shrink tubing, other any other material which would seal the cap and provide an efficacious attachment to the fiber. The outer securing element can be stainless steel, shrink tubing, polymeric material, or any other suitable flexible or rigid material.

The attaching means, i.e. the combination of bushing and optional adhesive, is but one possible attachment means possible. It will be apparent to one skilled in the art that numerous embodiments of the above described bushing connection between the cap and the optical fiber are possible. Other combinations might include shrink tubing, chemical bonds, compression fittings, fused elements, etc. An important feature of the present embodiments is the low profile design. There is a smooth transition between the proximal end of the cap and the optical fiber. This allows the fiber and cap assembly to be inserted through a lumen of an endoscope conveniently without encountering difficulty and preventing visual observation thereof. It is important to remember that the drawings are not necessarily drawn to scale for all embodiments possible.

The transparent cap can be made out of quartz or some other material. A typical length of the transparent cap portion would be 0.60 inches and might have an outside diameter of 0.06 inches. Typical fibers used in the assembly would be 500–1000 microns in diameter. It will be understood that the dimensions listed herein are merely representative of the preferred embodiment. Modifications and improvements in the connection between the cap and fiber and materials used therein will be obvious to those skilled in the art.

Figure 3:
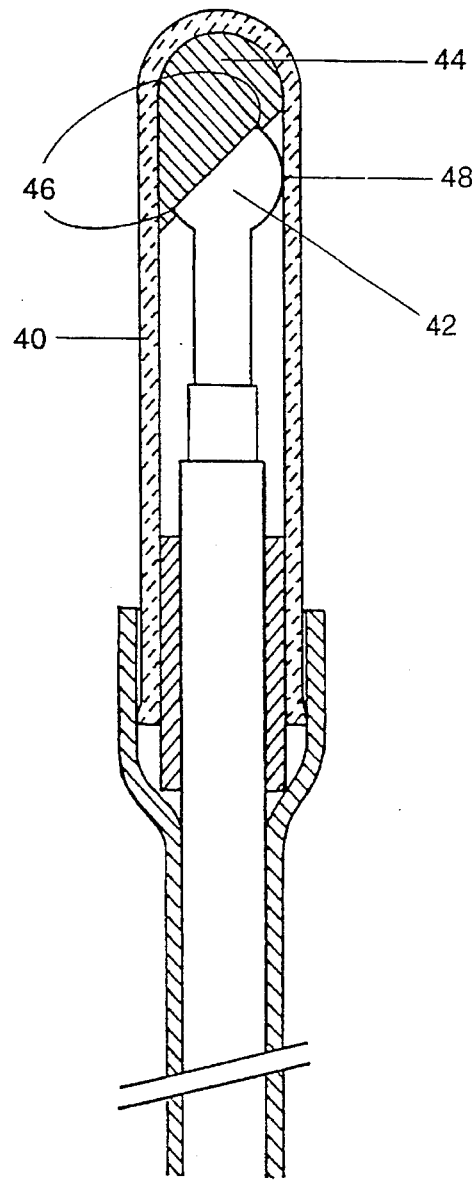
FIG. 3 is a cross section view of the transmitting end of another preferred embodiment of the invention, specifically showing the transparent cap over the ball tip fiber end with the transmitting end of the fiber buried in the reflective insert.

FIG. 3 is a cross section view of the transmitting end of another preferred embodiment of the invention, specifically showing the transparent cap 40 over the ball tip fiber end 42 with the transmitting end of the fiber buffed in the reflective insert 44. One way to make this truncated ball shaped tip would be to heat the end of a silica fiber. As the tip starts to melt, the molten silica will coalesce at the end and form a ball or drop of molten silica. The ball tip is then cut and polished at an appropriate angle. Shown at 46 is a recess in the reflective surface into which the polished bias cut end surface of the optical fiber is placed. By inserting the end of the fiber into this recess there is even greater efficiency in transmission of the laser radiation off of the reflective surface. Radiative loss due to beam scattering or leakage is reduced to a minimum and the tip will transmit the laser radiation without overheating and losing mechanical or optical integrity Furthermore, by providing a ball at the end of the fiber, the cross sectional area of the reflected beam will be greater, an embodiment which can be selected for specific purposes. When the ball tip is placed into the transparent cap against the reflective insert there would be a minimum of a single contact point 48 between the ball tip and the transparent cap during the manufacturing process the firing tip is heated, from either the inside of the cap or from the outside. This contact point becomes a fusion point between the ball tip and the cap. Thus, the ball tip fiber becomes fused to the inside of the cap and will remain so fused during the operation of the fiber. This improvement over the existing technology allows the radiation being transmitted through the tip to pass through, effectively, a single, continuous path. This fusion point eliminates the interface between the end of the fiber tip and the inside of the cap, allowing the laser beam, once produced and coupled to an optical fiber, to be directed to the intended site without experiencing refraction at any other point than upon exiting the device. This increases the efficiency of transmission by reducing the optical path traveled by the radiation to that with the maximum purity possible, a single, contiguous, undisrupted optical path. The connecting means for attaching the transparent cap over the metal insert is fairly similar to that shown in FIG. 2, and additional various modifications and versions will be obvious.

Figure 4:
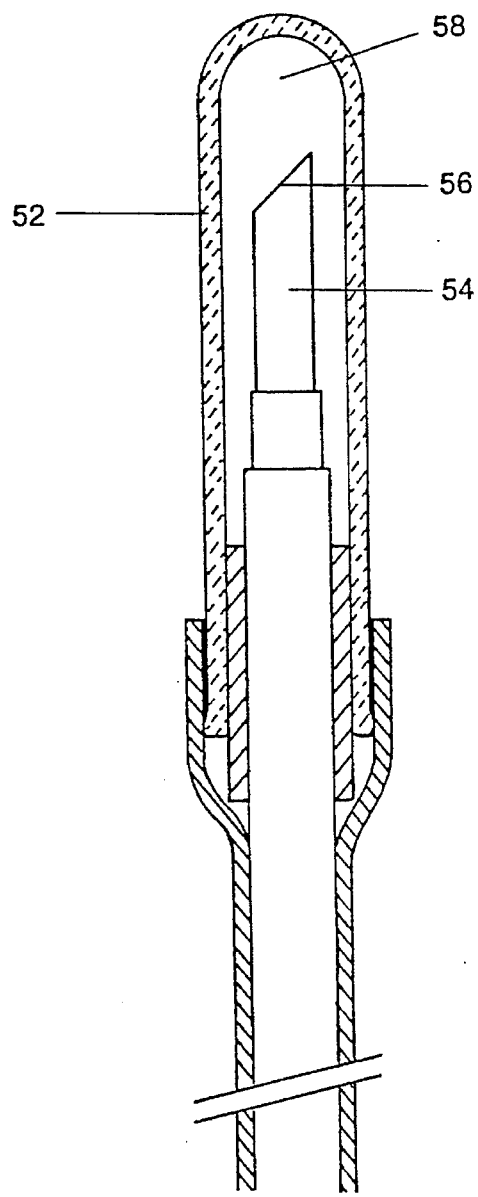
FIG. 4 is a cross section view of the transmitting end of a preferred embodiment of the invention, showing specifically the transparent cap over a bias cut fiber.

FIG. 4 shows a cross section view of the transmitting end of a preferred embodiment of the invention, showing specifically the transparent cap over a bias cut fiber. As shown, the cap 52 is fitted over the distal end of the optical fiber 54. The tip of the fiber 56 has been cut and polished. In these embodiments there is no reflective insert placed against the tip of the fiber, as in those shown in FIGS. 2 and 3. Instead, there is a chamber 58 which is created in the distal tip of the transparent cap. This chamber can be evacuated, filled with air or any other suitable fluid, liquid or gas which would result in beam reflection or refraction at desired or predetermined angles. In these embodiments, the difference between the index of refractivity of the quartz material of the optical fiber and the fluid filling the chamber and the transparent cap and the surrounding fluid or other operating environment of the device will result in a certain angle of refractance of the transmitted laser radiation.

Figure 5:
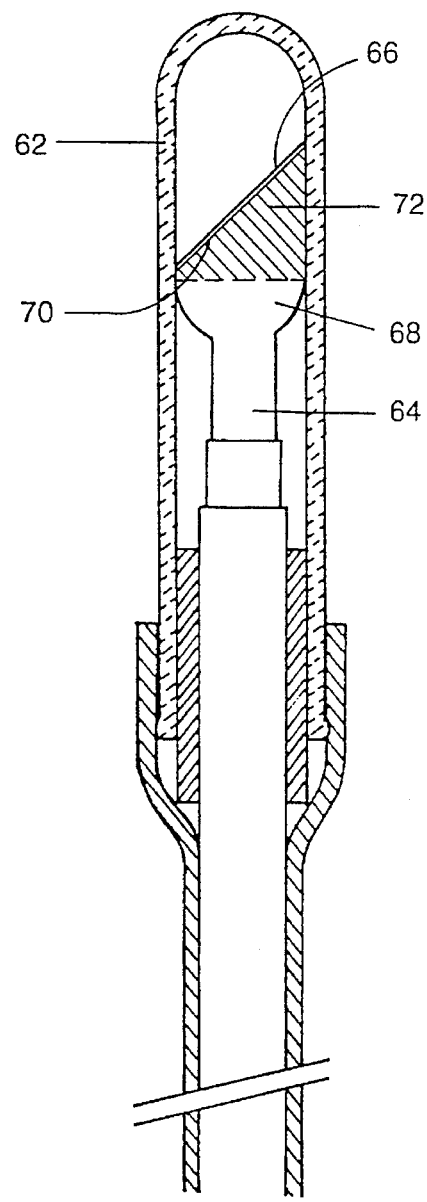
FIG. 5 is a cross section view of the transmitting end of a preferred embodiment of the invention, showing specifically the transparent cap over a bias cut fiber with a reflective layer applied to the transmitting end of the fiber.

FIG. 5 is a cross section view of the transmitting end of a preferred embodiment of the invention, showing specifically the transparent cap 62 over an optical fiber 64 with a reflective layer 66 applied to the transmitting end of the fiber. The distal tip 68 of the fiber has been formed into an elongated ball tip and the end surface 70 has been given a bias cut. In this embodiment, the outside diameter of the elongated ball tip is very close to the inside diameter of the transparent cap. Thus, during the manufacturing process, heat applied from either the inside or outside of the transparent cap can cause fusion between the tip of the fiber and the inside of the cap. Thus, rather than a fusion point being formed at a single point, as in FIG. 3, there would be a zone of fusion between the entire elongated ball tip portion of the fiber and the inside of the cap, as represented by the shaded portion 72, or portions thereof. It is not necessary that the entire cylindrical portion of the elongated and bias cut fiber tip be fused together all the way around the fiber tip circumferentially. Rather, the main area of interest is that through which the laser beam will travel, i.e. an undisrupted optical path. The reflectance or refractance of the laser beam would still occur at the bias cut end surface of the fiber.

As shown, a layer of some reflective material could be, but need not be, applied to this bias cut end surface. As shown in FIG. 4, the bias cut end surface of the fiber need not necessarily be coated with a reflective or interference layer, but could be left clean and polished. The material of the coating could be a dielectric, a metal or some type of interference film or layer or layers. A layer of gold would be one material which would provide a very highly reflective surface and would result in nearly complete transmission of the incident radiation. In this embodiment, the laser beam would be reflected and may also experience refraction at the fiber/reflective layer interface.

Figure 6C:
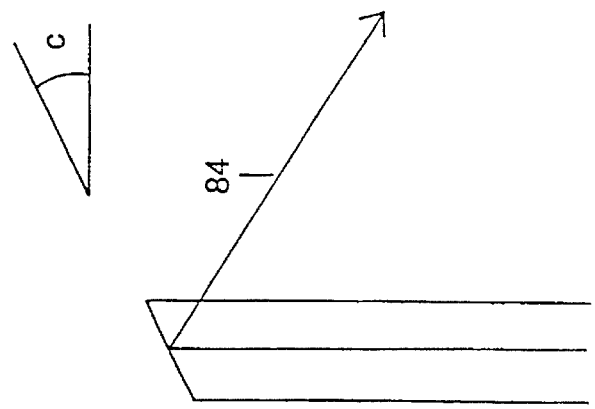
FIGS. 6A, 6B and 6C show cross sectional views of the bias cut end surface of the optical fiber whereby the end surface lies in a plane approximately equal to, greater than and less than, respectively, 45 degrees, with respect to the central axis of the fiber.
Figure 6B:
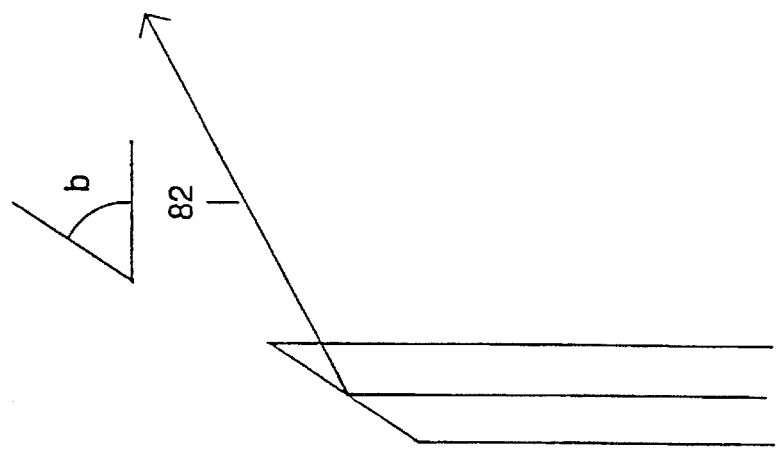
Figure 6A:
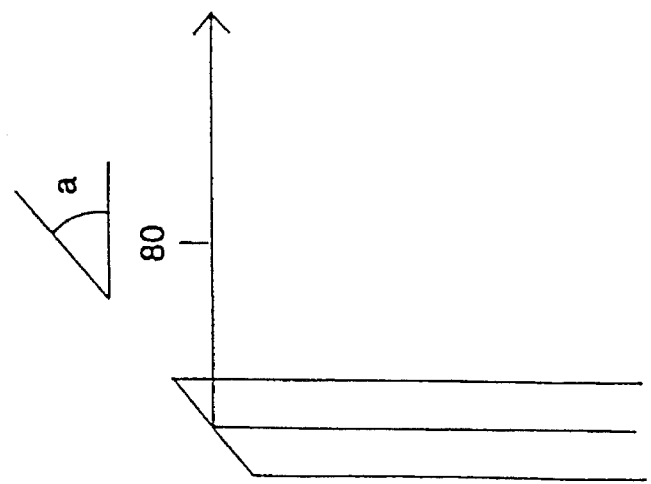

FIGS. 6A, 6B and 6C show cross sectional views of the bias cut end surface of the optical fiber whereby the end surface lies in a plane approximately equal to, greater than and less than, respectively, 45 degrees, with respect to the central axis of the fiber. In FIG. 6A the resultant beam path 80 is reflected to an angle of approximately 90 degrees with respect to the central axis of the fiber because the end surface lies in a plane at an angle a of approximately 45 degrees. In FIG. 6B the resultant beam path 82 is reflected to an angle greater than 90 degrees with respect to the central axis of the fiber because the end surface lies in a plane at an angle b which is greater than 45 degrees. In FIG. 6C the resultant beam path 84 is reflected to an angle less than 90 degrees with respect to the central axis of the fiber because the end surface lies in a plane at an angle c which is less than 45 degrees. Almost any of the embodiments of this invention, including those shown in FIGS. 1 through 5, can be constructed so as to deliver laser radiation to a wide range of predetermined angles. However, based on the characteristics of the fiber and the reflective surface, or other media surrounding the tip of the fiber inside the sealed chamber of the transparent cap, there will be maximum and minimum angles for the bias cut end surface, outside of which the device will not function properly. If the angle of the bias cut end surface is too great with respect to the central axis of the fiber, then the laser energy may be refracted through the fiber both ways, rather than being all directed in one direction relative to the bias cut end surface. If the bias cut end surface is at an angle too small, then the reflected laser beam will be partially reflected backward, internally, and may have a destructive impact on the firing tip. Some of the laser beam would pass straight through the device, or directly impinge upon the reflective surface or insert and cause rapid thermal increase and failure during operation. Additionally, at angles other than somewhat greater than 45 degrees or somewhat less than 45 degrees, the efficiency of the reflection will decrease resulting in greater heat absorption by the firing tip and less efficient cauterizing, coagulating and ablating. Nevertheless, there is a wide range of angles at which the laser beam can be reflected to efficiently and precisely, both greater than and less than precisely transverse to the central axis of the optical fiber.

The embodiments of this invention can be used in almost all surgical operations for ablating, coagulating, incising or otherwise removing tissue. The different embodiments disclosed in the invention are also suitable for use in scientific, industrial, entertainment, communications and other commercial applications where angle delivery of laser beams at any wavelength via optical fibers is useful and applicable.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A transparent cap fiber optic laser beam angle delivery device, said device comprising:
    an optical fiber, said fiber having:
        a receiving end,
        a central axis, and
        a transmitting end, said transmitting end having a bias cut end surface, said bias cut end surface defining a predetermined operative angle with said central axis of said fiber;
    a transparent cap, said transmitting end disposed within said transparent cap such that said transmitting end of said optical fiber is protected from exposure to operating debris and fluids; and
    an attaching means, said attaching means securing said transparent cap to said fiber.

2. The invention of claim 1 wherein said transparent cap is made of quartz.

3. The invention of claim 1 wherein said transparent cap is made of a polymeric material.

4. The invention of claim 1 wherein said transparent cap is made of a material which allows the transmission of laser radiation.

5. The invention of claim 1 wherein said end surface lies in a plane at an angle of approximately 45 degrees to said central axis.

6. The invention of claim 1 wherein said end surface lies in a plane at an angle greater than 45 degrees with respect to said central axis.

7. The invention of claim 1 wherein said end surface lies in a plane at an angle less than 45 degrees with respect to said central axis.

8. The invention of claim 1 wherein said bias cut end surface of said fiber is contoured such that a beam with a predetermined beam pattern is delivered.

9. The invention of claim 1 wherein said attachment means creates a sealed chamber within said cap within which said bias cut end surface is disposed.

10. The invention of claim 1 wherein said chamber is filled with a fluid.

11. The invention of claim 1 wherein said chamber is filled with a gas.

12. The invention of claim 1 wherein said chamber is evacuated.

13. The invention of claim 1 wherein a reflective coating is applied over said bias cut end surface of said transmitting end of said optical fiber.

14. The invention of claim 13 wherein said reflective coating consists of a dielectric material.

15. The invention of claim 13 wherein said reflective coating consists of a metallic material.

16. The invention of claim 13 wherein said reflective coating consists of a plurality of layers of different materials, said materials having different indices of refraction.

17. The invention of claim 13 wherein said fiber is enlarged proximate said transmitting end providing a truncated ball shaped transmitting end with a bias cut end surface with an increased area.

18. The invention of claim 13 wherein at least one point on said transmitting end of said optical fiber is in intimate contact with said transparent cap.

19. The invention of claim 18 wherein said transmitting end of said optical fiber is fused to said transparent cap providing an undisrupted optical path.

20. The invention of claim 1 wherein said transparent cap further comprises an insert member having a reflective surface.

21. The invention of claim 20 wherein said bias cut end surface of said optical fiber is in intimate contact with said reflective surface of said insert member.

22. The invention of claim 20 wherein said insert member is composed of a metallic material.

23. The invention of claim 20 wherein said fiber is enlarged proximate said transmitting end providing a truncated ball shaped transmitting end with a bias cut end surface with an increased area.

24. The invention of claim 23 wherein said reflective surface of said insert is provided with a recess such that said bias cut end surface of said fiber is disposed within said recess.

25. The invention of claim 23 wherein at least one point on said truncated ball shaped transmitting end is in intimate contact with said transparent cap.

26. The invention of claim 25 wherein said transmitting end of said optical fiber is fused to said transparent cap providing an undisrupted optical path.

27. The invention of claim 20 wherein said fiber is enlarged proximate said transmitting end providing an elongated ball shaped transmitting end with a bias cut end surface with an increased area.

28. The invention of claim 27 wherein said reflective surface of said insert is provided with a recess such that said bias cut end surface of said fiber is disposed within said recess.

29. The invention of claim 27 wherein at least one point on said elongated ball shaped transmitting end is in intimate contact with said transparent cap.

30. The invention of claim 29 wherein said transmitting end of said optical fiber is fused to said transparent cap providing an undisrupted optical path.

31. The invention of claim 23 wherein said reflective surface of said insert is provided with a recess such that said bias cut end surface of said fiber is disposed within said recess.

32. The invention of claim 1 wherein said fiber is enlarged proximate said transmitting end providing a truncated ball shaped transmitting end with a bias cut end surface with an increased area.

33. The invention of claim 32 wherein at least one point on said truncated ball shaped transmitting end is in intimate contact with said transparent cap.

34. The invention of claim 33 wherein said transmitting end of said optical fiber is fused to said transparent cap providing an undisrupted optical path.

35. The invention of claim 1 wherein said fiber is enlarged proximate said transmitting end providing an elongated ball shaped transmitting end with a bias cut end surface with an increased area.

36. The invention of claim 35 wherein at least one point on said elongated ball shaped transmitting end is in intimate contact with said transparent cap.

37. The invention of claim 36 wherein said transmitting end of said optical fiber is fused to said transparent cap providing an undisrupted optical path.

38. The invention of claim 1 wherein said fiber is enlarged proximate said transmitting end providing an elongated ball shaped transmitting end with a bias cut end surface with an increased area.

39. The invention of claim 1 wherein said attaching means comprises a bushing disposed between said transparent cap and said optical fiber.

40. The invention of claim 1 wherein said attachment means is composed entirely out of flexible materials.

41. The invention of claim 1 wherein at least one point on said transmitting end of said optical fiber is in intimate contact with said transparent cap.

42. The invention of claim 41 wherein said transmitting end of said optical fiber is fused to said transparent cap providing an undisrupted optical path.

* * * * *